(12) United States Patent
Stribling

(10) Patent No.: US 7,850,613 B2
(45) Date of Patent: Dec. 14, 2010

(54) APPARATUS AND METHOD FOR THREE DIMENSIONAL ULTRASOUND BREAST IMAGING

(75) Inventor: Mark L. Stribling, Johnson City, TN (US)

(73) Assignee: Orison Corporation, Johnson City, TN (US)

( * ) Notice: Subject to any disclaimer, the term of this patent is extended or adjusted under 35 U.S.C. 154(b) by 556 days.

(21) Appl. No.: 10/852,398

(22) Filed: May 24, 2004

(65) Prior Publication Data

US 2004/0254464 A1 Dec. 16, 2004

Related U.S. Application Data

(60) Provisional application No. 60/474,687, filed on May 30, 2003.

(51) Int. Cl.
*A61B 8/14* (2006.01)
(52) U.S. Cl. .................. 600/459; 73/644; 128/915; 600/437; 600/439
(58) Field of Classification Search .............. 600/459, 600/437, 439; 601/2–4; 73/644; 128/915
See application file for complete search history.

(56) References Cited

U.S. PATENT DOCUMENTS

| | | | |
|---|---|---|---|
| 3,480,002 A | 11/1969 | Flaherty et al. | |
| 3,765,403 A | 10/1973 | Brenden | |
| 3,964,296 A | 6/1976 | Matzuk | |
| 4,341,222 A * | 7/1982 | Gardineer et al. | 600/437 |
| 4,537,074 A | 8/1985 | Dietz | |
| 4,545,385 A * | 10/1985 | Pirschel | 600/445 |
| 4,888,746 A | 12/1989 | Wurster et al. | |
| 5,042,492 A | 8/1991 | Dubut | |
| 5,301,168 A | 4/1994 | Miller | |
| 5,485,842 A | 1/1996 | Quistgaard | |
| 5,535,751 A | 7/1996 | Raz | |
| 5,677,491 A | 10/1997 | Ishrak et al. | |
| 5,706,820 A | 1/1998 | Hossack et al. | |
| 5,740,806 A | 4/1998 | Miller | |
| 5,792,058 A | 8/1998 | Lee et al. | |
| 5,797,845 A | 8/1998 | Barabash et al. | |
| 5,810,742 A * | 9/1998 | Pearlman | 600/547 |
| 5,840,032 A | 11/1998 | Hatfield et al. | |
| 5,865,750 A | 2/1999 | Hatfield et al. | |

(Continued)

OTHER PUBLICATIONS

Anon, SonoSite TITAN(tm) System Specifications, product brochure, SonoSite, Inc., copyright 2003.

(Continued)

*Primary Examiner*—Long V Le
*Assistant Examiner*—Ellsworth Weatherby
(74) *Attorney, Agent, or Firm*—Peter J. Manso; Edwards Angell Palmer & Dodge LLP

(57) ABSTRACT

An apparatus for ultrasonic mammography includes: an array of ultrasonic transducers and signal processing means for converting the output of the transducer array into three dimensional renderings of anatomical features; and, an applicator device having a first side conformable to the contour of the transducer array and a second side configured to accept the breast, the applicator device further containing a quantity of fluid sufficient to surround and stabilize the breast during examination without substantially altering the breast from its natural shape.

49 Claims, 5 Drawing Sheets

U.S. PATENT DOCUMENTS

| | | | |
|---|---|---|---|
| 5,882,309 A | | 3/1999 | Chiao et al. |
| 5,897,501 A | | 4/1999 | Wildes et al. |
| 5,956,292 A | * | 9/1999 | Bernstein .................. 367/140 |
| 6,102,857 A | | 8/2000 | Kruger |
| 6,102,860 A | | 8/2000 | Mooney |
| 6,117,080 A | * | 9/2000 | Schwartz .................. 600/443 |
| 6,183,419 B1 | | 2/2001 | Wildes |
| 6,390,981 B1 | | 5/2002 | Jago |
| 6,409,668 B1 | * | 6/2002 | Wollschlaeger ............ 600/443 |
| 6,478,739 B1 | * | 11/2002 | Hong ........................ 600/437 |
| 6,511,426 B1 | | 1/2003 | Hossack et al. |
| 6,511,433 B1 | * | 1/2003 | Benjamin ................. 600/463 |
| 6,618,206 B2 | | 9/2003 | Tarakci et al. |
| 6,786,868 B2 | * | 9/2004 | Stotzka et al. ............. 600/437 |
| 6,899,696 B2 | * | 5/2005 | Morton et al. ............... 604/74 |
| 2002/0120195 A1 | | 8/2002 | Hossack et al. |
| 2003/0007598 A1 | * | 1/2003 | Wang et al. .................. 378/37 |
| 2003/0076599 A1 | | 4/2003 | Tarakci et al. |
| 2003/0085635 A1 | | 5/2003 | Davidsen |
| 2004/0002435 A1 | | 1/2004 | Petersen et al. |
| 2004/0002652 A1 | | 1/2004 | Phelps et al. |
| 2004/0002656 A1 | | 1/2004 | Sheljaskow et al. |
| 2004/0004906 A1 | | 1/2004 | Vernet et al. |
| 2004/0044284 A1 | | 3/2004 | Von Behren et al. |
| 2004/0122321 A1 | | 6/2004 | Alexandru |
| 2004/0254464 A1 | | 12/2004 | Stribling |
| 2005/0054958 A1 | | 3/2005 | Hoffmann |
| 2006/0235300 A1 | | 10/2006 | Weng et al. |

OTHER PUBLICATIONS

Anon, Understanding Ultrasound, tutorial paper from SonoSite web site, copyright 2003.

Anon, Silicon Ultrasound, www.sensant.com/pro_advDiag.html, available at least as early as May 27, 2003.

Ladabaum et al. Surface Machined Capacitive Ultrasonic Transducers, IEEE Trans. Ultrasonics, Ferroelectrics, and Freq. Control vol. 45 No. 3, May 1998.

Cittadine, MEMS Reshapes Ultrasonic Sensing, Flow Control, the Magazine of Fluid Handling Systems, Nov./Dec. 2001.

Ramamurthy et al., "Whitepaper: ACUSON Sequoia Ultrasound Platform Compound Imaging Technologies," Siemens Medical Solutions USA, Inc., Ultrasound Division, Mountain View CA, 8 pages (2004).

Thomenius, "Evolution of Ultrasound Beamformers," 1996 IEEE Ultrasonics Symposium 1615-1622 (1996).

* cited by examiner

APPARATUS AND METHOD FOR THREE DIMENSIONAL ULTRASOUND BREAST IMAGING

CROSS REFERENCE TO RELATED APPLICATIONS

This application claims the benefit of Provisional Patent Application Ser. No. 60/474,687 filed by the present inventor on May 30, 2003, the entire disclosure of which is incorporated herein by reference.

BACKGROUND OF THE INVENTION

1. Field of the Invention

This invention pertains to the field of ultrasonic medical imaging, and more particularly to systems and methods for diagnostic imaging of the breast. More specifically the invention describes a coupling device for an ultrasonic imaging transducer that stabilizes the breast to allow rapid examination of the patient while accommodating anatomical variations, maximizing cleanliness, and minimizing patient discomfort.

BACKGROUND

2. Discussion of Prior Art

Mammography is a well-known medical procedure used to diagnose various abnormalities such as cysts, calcifications, and tumors. The standard procedure involves compressing the breast along vertical and horizontal planes and taking radiographs through the tissue. The method is generally uncomfortable to the patient and exposes the patient to X-ray radiation. Furthermore, it is well known that the method is less effective at finding abnormalities in areas where the breast tissue is particularly dense.

Ultrasound imaging has emerged as an alternative method for examining selected areas of the body, including the breast. Various methods have been described for configuring the transducers, analyzing the data therefrom, and providing an acoustic interface with the patient.

U.S. Pat. No. 3,765,403 by Brenden describes immersion of the breast in a fluid tank, and further includes a clamping device to compress the breast during examination. The fluid tank of '403 further includes ultrasonic lenses and other features to enable holographic images to be created.

U.S. Pat. No. 3,480,002 by Flaherty et al. describes a mechanically scanned transducer in a liquid filled tank with a flexible bottom that is brought into contact with the patient. The patient must be greased with couplant to ensure good transmission of the signal from the flexible tank. It will be appreciated that the bottom of the flexible tank would need to be cleaned after each patient.

U.S. Pat. No. 3,964,296 by Matzuk describes various means for coupling an ultrasonic transducer to the patient. Specifically in FIG. 31 and the corresponding discussion at Col. 30 Lines 15-55, Matzuk describes a substantially solid elastomer body with a cavity approximating the size and shape of the breast. The breast is inserted into the cavity and the ultrasound is introduced from the opposite side of the elastomer body. Grease or other couplant would be applied to the patient in order to achieve good sonic transmission between the elastomer and the breast. The internal cavity of the elastomer body would need to be thoroughly cleaned after each patient and it will be further appreciated that a single applicator would not be able to accommodate large variations in patient anatomy. Therefore, a large number of applicators of various sizes would be required and the technician would need to select the one that presents the best fit for a particular patient.

Various hand-held ultrasonic devices are available commercially. Products such as the SonoSite TITAN™ system are typical of the art. By the nature of their construction and operation, the use of these devices tends to be laborious and generally confined to localized examination of a particular area of interest. Grease or other couplant must be applied to the device and to the patient. It will be appreciated that modern medical practices are expected to maintain rigorous standards of cleanliness to avoid transfer of pathogens from one patient to the next. An ultrasonic transducer with a layer of viscous couplant that has been in contact with a patient's skin must therefore be thoroughly cleaned before the next use.

OBJECTS AND ADVANTAGES

Objects of the present invention include the following: providing a mammography system that does not expose the patient to ionizing radiation; providing an ultrasonic mammography system that can accommodate wide variations in patient anatomy; providing a mammography system that creates less patient discomfort; providing a mammography system with improved capability to image features in dense tissue; providing a three dimensional imaging ultrasonic transducer system with a separate means for acoustic coupling to the patient; providing a method for stabilizing the breast during imaging while minimizing physical distortion of the tissues under examination; and, providing a disposable coupler for an ultrasonic transducer so that the transducer does not require cleaning after examining a patient. These and other objects and advantages of the invention will become apparent from consideration of the following specification, read in conjunction with the drawings.

SUMMARY OF THE INVENTION

According to one aspect of the present invention, an apparatus for ultrasonic mammography includes: an array of ultrasonic transducers and signal processing means for converting the output of the transducer array into three dimensional renderings of anatomical features; an applicator device having one end that is conformable to the contour of the transducer array and the other end configured to accept the breast along with a quantity of fluid sufficient to surround and stabilize the breast during examination without substantially altering the breast from its natural shape; and, optionally, a viscous couplant layer disposed between the transducer array and the applicator device and an adhesive layer between the applicator device and the breast.

According to another aspect of the present invention, a method for ultrasonic mammography includes the following steps: configuring an array of ultrasonic transducers and signal processing means to create three dimensional renderings of anatomical features in a human breast; placing one end of an applicator device into contact with said transducer array, optionally using a viscous couplant layer between the applicator and the transducer array; placing the breast into the other end of the applicator device and filling the remaining volume of the device with a fluid, whereby the fluid eliminates air gaps and provides a more efficient path for ultrasonic signals into and out of the breast during examination and the applicator device stabilizes the breast during data acquisition without substantially deforming the breast from its natural shape.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting embodiments illustrated in the drawing figures, wherein like numerals (if they occur in more than one view) designate the same elements. The features in the drawings are not necessarily drawn to scale.

DETAILED DESCRIPTION OF THE INVENTION

Figure 1:
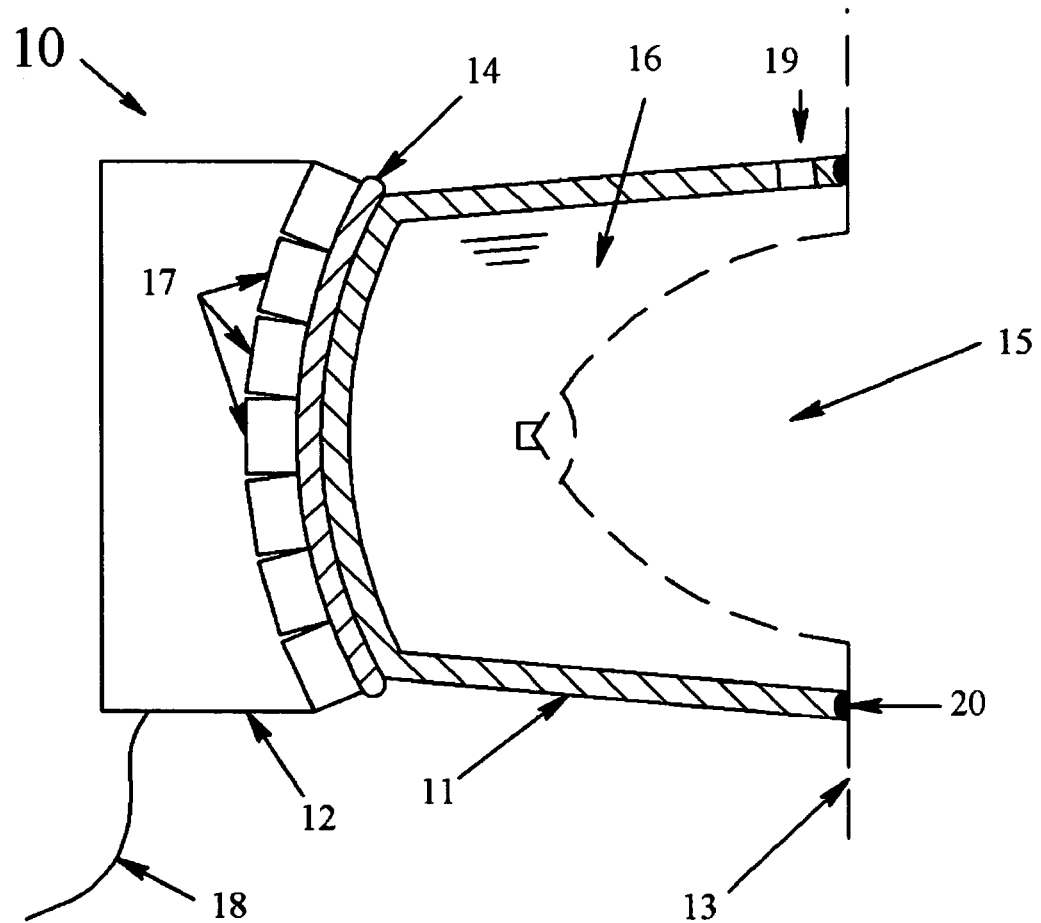
FIG. 1 is a schematic diagram, shown in cross section, of one embodiment of the invention, in which the ultrasonic transducer assembly has a substantially concave surface.

In its most general embodiment, the invention comprises three basic elements: first, an ultrasonic transducer array capable of generating signals that may be analyzed to produce three-dimensional sonograms; second, an electronic analysis system to convert the ultrasonic signals into various imaging data sets in conjunction with an electronic user interface; and third, an applicator device, preferably disposable, configured to provide good acoustic coupling to breasts of various sizes while eliminating the need to expose the transducer to repeated cleaning.

Ultrasonic transducers may be designed in various ways, and the present invention is not limited to any particular transducer design but rather may be advantageously applied to adapt many different types of transducers to the problem of breast imaging. Transducer arrays may be curved, with the front surface typically concave, and the individual piezoelectric elements may be substantially square blocks such as described by P. Dubut in U.S. Pat. No. 5,042,492. Concave arrays may also be constructed with annular elements, such as that described by Dietz in U.S. Pat. No. 4,537,074. Combining several linear arrays to produce an electronically scanned ultrasonic "pencil" beam from crossed flat acoustic beams is described by Barabash et al. in U.S. Pat. No. 5,797,845. More recently, a new type of acoustic transducer has been developed in which silicon micromachining techniques are used to fabricate suspended membranes that are excited capacitively, as described in detail by Ladabaum et al. ("Surface Micromachined Capacitive Ultrasonic Transducers," IEEE Trans. on Ultrasonics, Ferroelectrics, and Freq. Control, Vol. 45, No. 3, May 1998). Silicon micromachined transducers for medical applications are available from Sensant Corp., 14470 Doolittle Dr., San Leandro, Calif. 94577.

Skilled artisans have long understood the need to achieve good acoustic coupling between the transducer and the object under examination. To this end, viscous materials, called couplants, are placed between the transducer and the patient to eliminate any air gap and replace it with an interface whose acoustic impedance is better matched to the transducer. As shown at 10 in FIG. 1, in one embodiment the present invention provides an applicator device in the form of a cup 11 that serves as a bridge between the transducer unit 12 and the patient 13 (indicated by dashed lines). An optional viscous couplant layer 14 may be disposed between the transducer and the applicator cup, and therefore does not come into direct contact with the patient. The applicator cup 11 is designed to receive the breast 15 during examination, and a fluid 16, preferably warm water, fills the volume between the cup and the breast, thereby acting as another acoustic couplant and also allowing for variations in patient anatomy. It will be understood that the applicator cup 11 may be provided in several different sizes to accommodate an even wider range in patient-to-patient variations.

Figure 2:
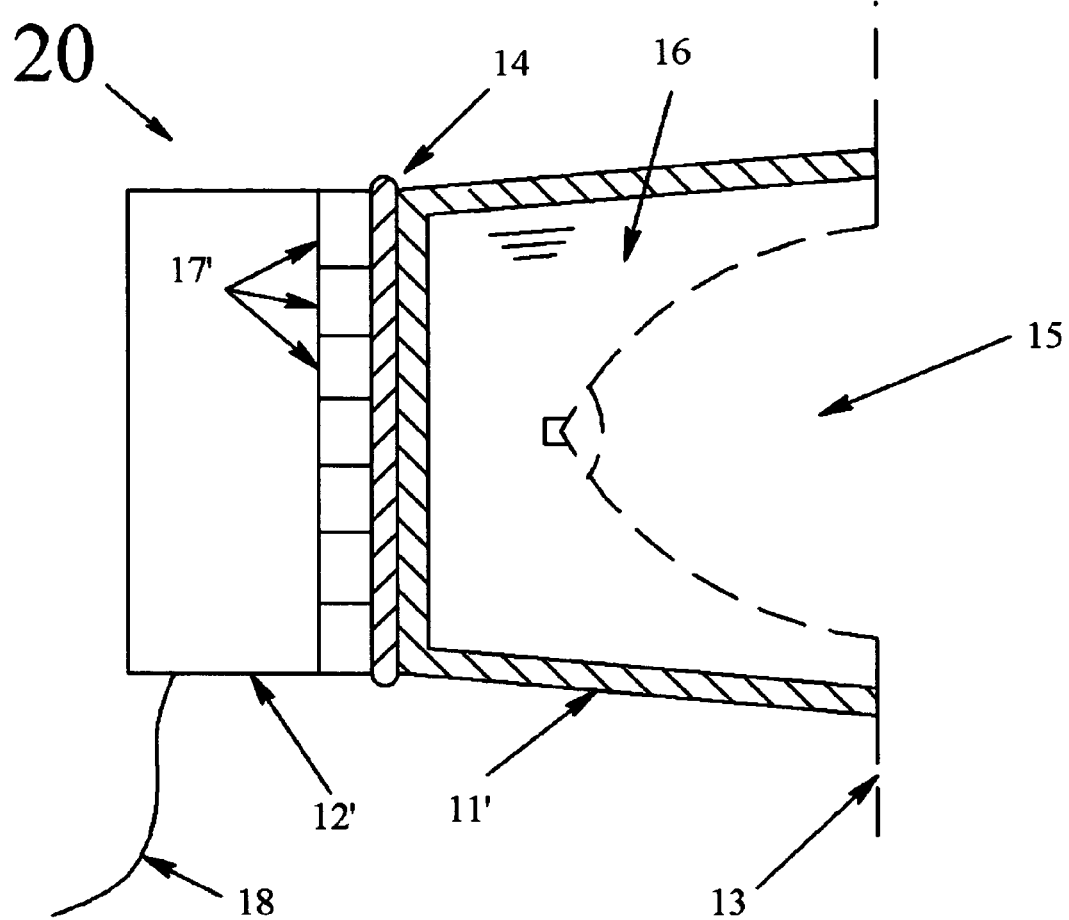
FIG. 2 is a schematic diagram, shown in cross section, of another embodiment of the invention, in which the ultrasonic transducer assembly has a substantially flat surface.

The applicator cup in FIG. 1 is configured for use with a transducer array 17 whose front surface is concave, whereas the cup 11' shown in FIG. 2 is adapted for a flat transducer array 17'. The basic operating principle is the same in either case, and it will further be understood that if a transducer has a curved face as shown in FIG. 1, the curvature may be convex or concave and may be generally cylindrical, spherical, parabolic, or other selected shape. The cup 11, 11' may be fabricated to whatever shape is appropriate for a particular transducer assembly. It will be further appreciated that in many instances the cup is preferably disposable after use on a single patient, and in such cases the cup is preferably fabricated from a low cost material such as various polymers. In other cases it might be desired to make the cup from a more durable material that may be cleaned and sterilized for later use on another patient.

As noted above, one purpose of the applicator cup 11, 11' is to stabilize the breast so that good three-dimensional renderings may be obtained quickly. It is therefore desirable that relative movement between the breast and the cup be minimal. As illustrated in the exemplary drawings, it is contemplated that in many cases there will likewise be little or no relative movement between the cup 11, 11' and the transducer array 12, 12'. However, Applicant recognizes that the inventive device may easily accommodate other ultrasonic techniques that might require relative movement between cup 11, 11' and transducer 12, 12'. For example, a linear array such as the SonoSite TITAN™ may be placed against cup 11, 11', utilizing a layer of couplant 14 and the transducer rocked or swept through a controlled angle or arc, thereby acquiring data that may be used to construct a three dimensional rendering of the tissue. For an application such as this, it will be appreciated that the back surface of the cup 11, 11' will be shaped such that it conforms to the path swept by the transducer during the aforedescribed rocking or sweeping motions. An alternative way to accommodate this motion is to make the backside of cup 11, 11' flexible or elastic so that its shape can follow the motions of the transducer while maintaining a fairly thin, uniform layer of couplant 14. Further means, such as a digital encoder, may be provided to detect the angular location of the transducer and provide this information to the ultrasonic apparatus so that accurate 3D images may be generated. Those skilled in the art will appreciate that the mechanical scanning of a linear transducer array and the electronic sweeping of a two-dimensional phased array are to some degree analogous operations and the inventive applicator device may therefore be used advantageously with either kind of transducer array.

An optional opening 19 may be provided through which the cup 11, 11' may be filled with liquid 16 after fitting to patient 13. An optional compliant sealing surface 20 may also be provided to further enhance fitting and patient comfort. The sealing surface 20 may be made in a number of familiar forms, including soft elastomer, a compressible elastomeric tube or O-ring, closed cell elastomeric foam, etc. Skilled artisans will appreciate that the cup 11, 11' may be oriented substantially horizontally, as shown, or it may be oriented vertically or at some other angle for maximal convenience to the patient and the practitioner.

A typical examination process using the inventive method may be carried out as follows: the patient is placed in a forward leaning position allowing the breast to be semi-pendulous, an applicator device is brought into contact with the breast and an air-free breast/applicator interface is maintained through an adhesive bond, vacuum pressure, or direct manual pressure, the transducer is brought into direct contact with the applicator device and the transducer/applicator interface is maintained by vacuum pressure, adhesive, couplant, or manual pressure. Residual space between the breast/applicator interface and the applicator/transducer interface may be occupied by adding fluid to the applicator device, thereby creating a more efficient path for ultrasonic signals into and out of said breast during examination.

Once the ultrasonic data is collected it is transferred electronically to the ultrasonic apparatus for analysis where a consolidated data set (volume of interest) is generated for each breast examined. This data set is electrically transferred to a computer for post image analysis using techniques well known in the art, including image enhancement, pixel mapping, thresholding, boundary detection, morphology, normalized correlation, geometric pattern matching, etc. The final images consisting of 2D and/or 3D representations of breast anatomy are presented on a monitor for radiological interpretation and diagnosis.

Figure 3:
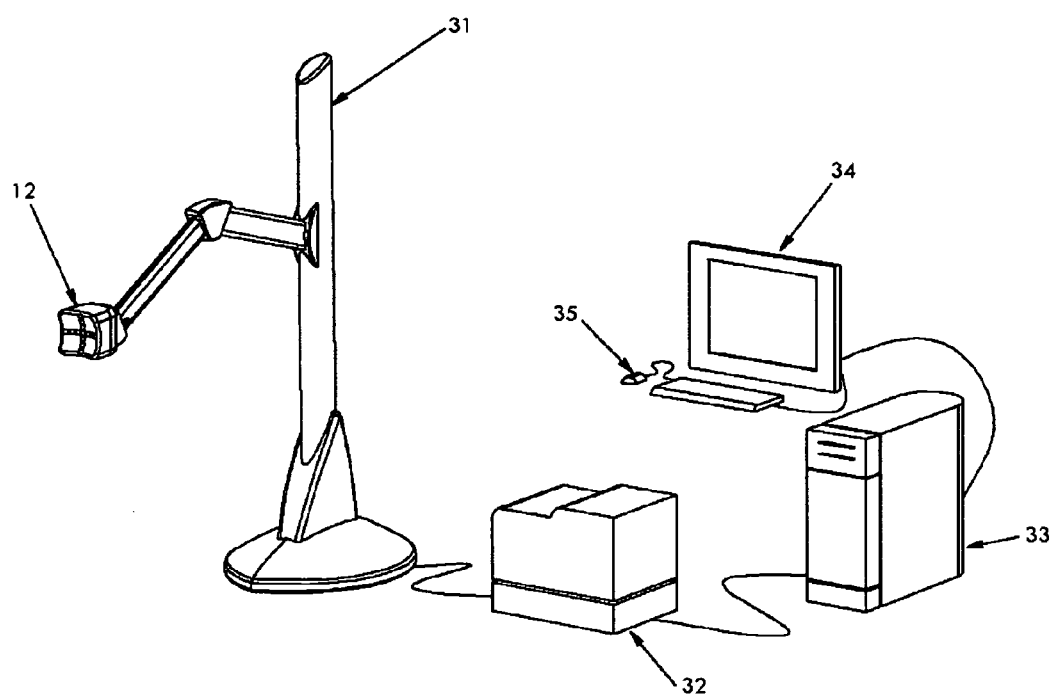
FIG. 3 is a schematic illustration of an ultrasonic imaging system adapted for mammography.

In the drawings, for simplicity, a simple transducer assembly 12, with a power/signal cable 18 is shown. It will be understood that the transducer unit may be hand-held or, as shown in FIG. 3, it may be supported on a mechanical linkage, boom, or stand 31 as are well known in the art. It will be further understood that the ultrasonic apparatus 32 may employ other modules, as shown schematically in FIG. 3, such as power supply, computer 33, monitor 34, user interface devices 35, etc., as are well known in the art. For example, the user interface may be configured to allow the user to select various operating modes such as pulsed-wave Doppler, color power Doppler, M-mode, 2D, tissue harmonic imaging, or other imaging modalities as are familiar to practitioners in the field. Various conventional means may be provided for capture and storage of the images for later retrieval and further analysis, typically via a dedicated personal computer. As used herein, the term image includes both single fixed images and images that form successive frames of a moving image.

The cup 11, 11' may incorporate other features to enhance its utility to the practitioner. For example, if different sizes of cups are available to accommodate wide ranges of anatomy, it might be desirable for the practitioner to document exactly which size or model of cup was used on a particular patient so that later examinations of that patient will be done consistently. To this end, the cup 11, 11' may contain various well-known means such as a stamped or molded part number or size, a printed bar code, wireless RFID tag, etc. The user interface may be adapted to read the bar code or RFID tag by conventionally known means, thereby incorporating this information along with the images and patient identification so that a more complete record of the procedure may be preserved. The actual exterior shape of the cup 11, 11', particularly the sidewalls, is of relatively minor importance to the functioning of the device. The cup may be generally cylindrical, tapered cylindrical, conical, rectangular, square, etc. It will be appreciated that a slight taper such as that shown in the drawings, is particularly useful because it will allow a large number of cups of any one size to stack together to minimize storage space. Alternatively, cups of various sizes may be stored in nesting fashion so that a range of sizes is readily available to the practitioner while requiring minimal storage space in the examining room.

Figure 4:
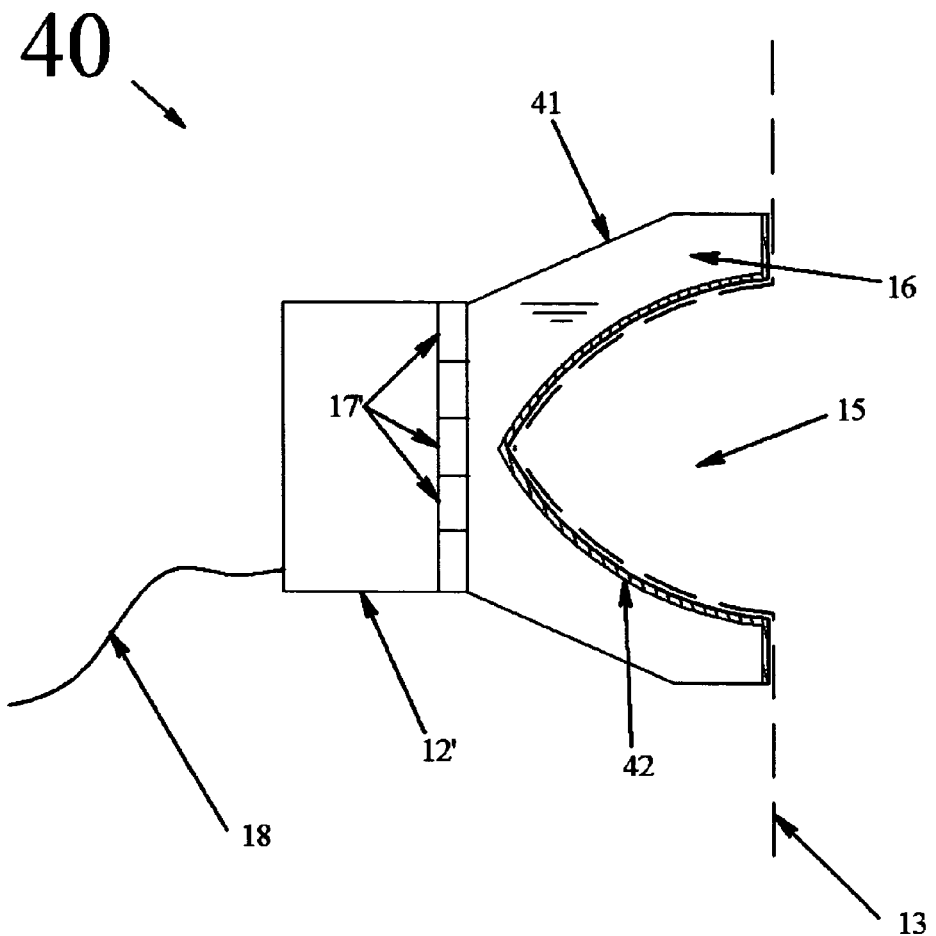
FIG. 4 is a schematic diagram, shown in cross section, of another embodiment of the invention, in which the applicator device is configured as a fluid-filled bag.
Figure 5:
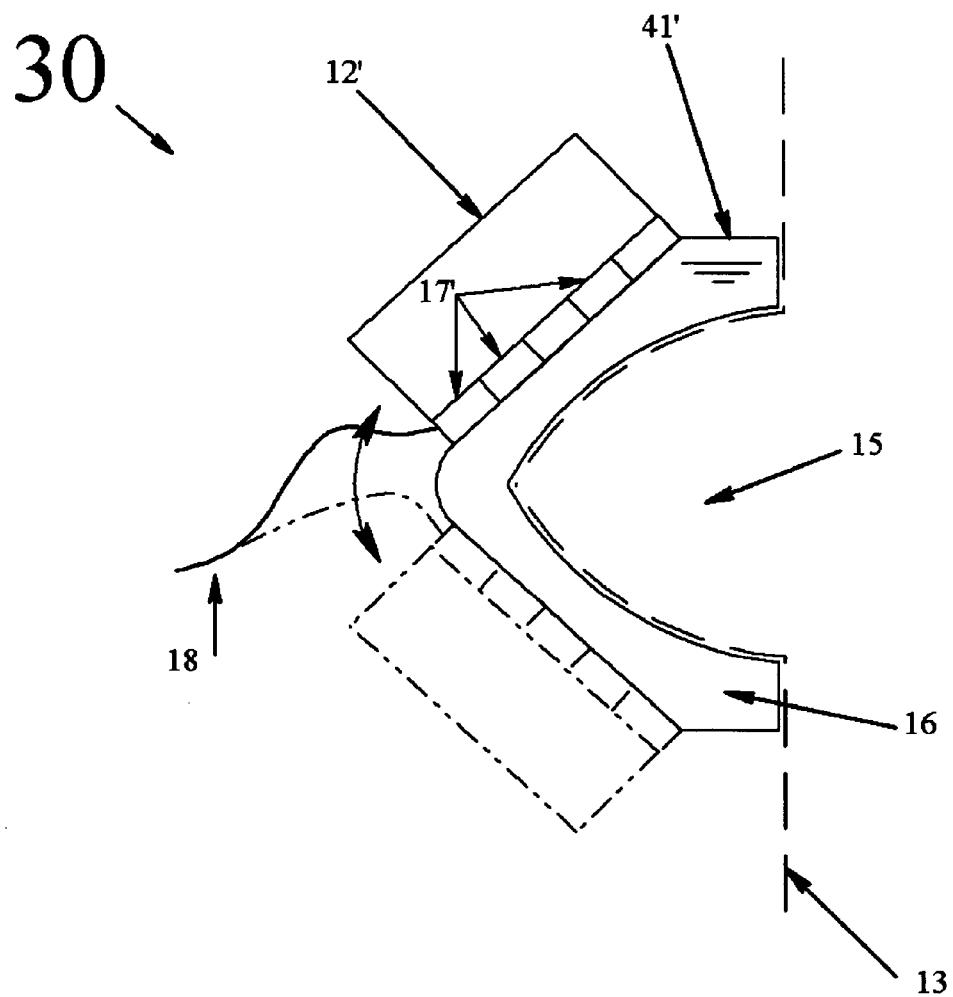
FIG. 5 is a schematic diagram, shown in cross section, of another embodiment of the invention, in which the applicator device is configured as a fluid-filled bag and a single transducer unit may be sequentially applied to more than one surface of the applicator device.

In another embodiment of the present invention, illustrated generally at 40 in FIGS. 4 and 30 in FIG. 5, the applicator device is supplied in the form of a flexible bag or pouch-like structure 41, 41', whose flexible nature allows it to conform, on the one side, to the patient's anatomy and conform, on the other side, to the front surface of the transducer assembly. An adhesive layer 42 is preferably applied to the side that faces the patient, whereby the bag 41 may be quickly applied to the breast so that it maintains good sonic coupling and eliminates air pockets. Fluid 16 is then introduced into the bag, further enhancing physical contact with the patient 13. The transducer assembly 12' is brought into contact with the bag 41, using either a partial vacuum or, optionally, a viscous couplant to maintain good sonic coupling between the transducer and the bag. It will be appreciated that such flexible bags will collapse to a very small volume when empty, thereby minimizing the space occupied during shipping, storage, and disposal.

In some instances, the acquisition of clear ultrasound images of the breast tissue may be adversely affected by "shadowing" from the nipple region. To address this situation, the inventive applicator device may alternatively be configured as shown in FIG. 5. In this configuration, the bag 41' has several surfaces that allow the ultrasonic signal from transducer 12' to be directed into the breast at an angle (rather than head-on), thereby avoiding shadowing by the nipple. In FIG. 5, two possible positions for the transducer 12' are shown, but those skilled in the art will appreciate that the bag 41' may be shaped so as to allow many possible positions of the transducer. In particular, the bag 41' may have a substantially conical surface, whereby the transducer assembly 12' may take any selected radial position around the general centerline of the breast.

The foregoing examples are provided to illustrate various aspects of the invention. Applicants do not intend for the invention to be limited to these exemplary embodiments, but rather to include all other modifications and variations of the invention that fall within the spirit and scope of the invention as defined by the following claims.

The invention claimed is:

1. An apparatus for ultrasonic mammography examination, said apparatus comprising:
   (a) a transducer unit having a plurality of ultrasonic transducers configured as a transducer array, the transducer array having a contour;
   (b) a signal processor for converting an output produced by the of said transducer array during an ultrasonic mammography examination into a rendering of one or more anatomical features of a breast of a patient;
   (c) an applicator device in a form of a cup having a first side and a second side, the first side, opposite or diagonal to the second side, being configured with a closed end conformable to the contour of the transducer array and the second side being configured with an open end to accept a breast of a patient within said applicator device for an ultrasonic mammography examination;
   wherein said applicator device is configured to receive a quantity of fluid sufficient to surround and stabilize a breast when the breast is fitted through the open end of the second side and positioned within said applicator device for an ultrasonic mammography examination without substantially altering the stabilized breast positioned within said applicator device from its natural shape during an ultrasonic mammography examination;

wherein the contour of the transducer array is disposed adjacent to the closed end of the first side of said applicator device during an ultrasonic mammography examination;

wherein the transducer array is external to said applicator device; and wherein minimal or no movement occurs between said applicator device and the transducer array during an ultrasonic mammography examination of the stabilized breast positioned within said applicator device.

2. The apparatus of claim 1, wherein the contour of the transducer array is substantially flat.

3. The apparatus of claim 1, wherein the contour of the transducer array is concave.

4. The apparatus of claim 1, wherein the ultrasonic transducers comprise devices fabricated from one of the group consisting of piezoelectric materials and capacitively actuated micro-machined silicon devices.

5. The apparatus of claim 1, wherein said applicator device is disposable.

6. The apparatus of claim 1, wherein said signal processor performs data set analysis using at least one algorithm selected from the group consisting of image analysis, image enhancement, pixel mapping, color space transform, time averaging, neighborhood operation, linear filtering, boundary detection, non-linear filtering, normalized correlation, and geometric pattern matching.

7. The apparatus of claim 1 wherein the fluid comprises water.

8. A method for ultrasonic mammography examination, said method comprising:
    (a) introducing a breast of a patient into an applicator device through a second portion of the applicator device to position the breast within the applicator device,
    wherein the applicator device is in a form of a cup and the second portion is configured with an open end to accept the breast within the applicator device for ultrasonic mammography examination,
    wherein the applicator device has a first portion located opposite or diagonal to the second portion,
    wherein the first portion is configured with a closed end and is positioned adjacent to a transducer array having a plurality of ultrasonic transducers,
    wherein the transducer array has a contour and is in operable communication with a signal processor for converting an output produced by the ultrasonic transducers during the ultrasonic mammography examination into a rendering of one or more anatomical features of the breast positioned within the applicator device,
    wherein the transducer array is external to the applicator device, and
    wherein the closed end of the first portion is conformable to the contour of the transducer array, so that the contour of the transducer array is disposed adjacent to the closed end of the applicator device;
    (b) introducing a fluid into the applicator device to (i) provide a continuous path for ultrasonic signals produced by the ultrasonic transducers to travel into and out of the breast positioned within the applicator device during the ultrasonic mammography examination, (ii) substantially fill a remaining volume within the applicator device and (iii) stabilize the breast positioned within the applicator device during data acquisition without substantially deforming the breast positioned within the applicator device from its natural shape during the ultrasonic mammography examination; and
    (c) conducting the ultrasonic mammography examination on the stabilized breast positioned within the applicator device to acquire data of the stabilized breast positioned within the applicator device for rendering one or more anatomical features of the stabilized breast positioned within the applicator device.

9. The method of claim 8, wherein the contour of the transducer array is substantially flat.

10. The method of claim 8, wherein the contour of the transducer array is concave.

11. The method of claim 8, wherein the ultrasonic transducers comprise devices fabricated from one of the group consisting of piezoelectric materials and capacitively actuated micro-machined silicon devices.

12. The method of claim 8, wherein the applicator device is disposable.

13. The method of claim 8, said method including the further step of:
    performing data set analysis of data of the stabilized breast positioned within the applicator device during the ultrasonic mammography examination using at least one algorithm selected from the group consisting of image analysis, image enhancement, pixel mapping, color space transform, time averaging, neighborhood operation, linear filtering, boundary detection, non-linear filtering, normalized correlation, and geometric pattern matching.

14. The method of claim 8, wherein the fluid comprises water.

15. The apparatus of claim 1, said apparatus further comprising a monitor for displaying a two dimensional or a three dimensional representation of the one or more anatomical features of the stabilized breast positioned within said applicator device, the representation being based on the rendering from the signal processor.

16. The method of claim 8, said method including the further step of:
    displaying a two dimensional or a three dimensional representation of the one or more anatomical features of the stabilized breast positioned within the applicator device, the representation being based on the rendering from the signal processor.

17. The apparatus of claim 1, said apparatus further comprising an acoustic coupling material disposed between the transducer array and said applicator device.

18. The method of claim 8, said method including the further step of:
    disposing an acoustic coupling material between the transducer array and the applicator device.

19. The apparatus of claim 1, said apparatus further comprising an adhesive layer disposed between at least a portion of the second side of said applicator device and the stabilized breast positioned within said applicator device.

20. The method of claim 8, said method including the further step of:
    disposing an adhesive layer between at least a portion of the second side of the applicator device and the stabilized breast positioned within the applicator device.

21. The apparatus of claim 1, wherein said applicator device is flexible so as to follow motions of the transducer array while maintaining acoustic coupling to the transducer array via an acoustic coupling layer.

22. The method of claim 8, wherein the applicator device is flexible so as to follow motions of the transducer array while maintaining acoustic coupling to the transducer array via an acoustic coupling layer.

23. The apparatus of claim 1, wherein the fluid is in direct contact with the stabilized breast positioned within said applicator device.

24. The apparatus of claim 23, said apparatus further comprising an elastomeric sealing surface sealing the cup to skin near the stabilized breast positioned within said applicator device.

25. The method of claim 8, said method including the further step of:
directly contacting the breast positioned within the applicator device with the fluid to stabilize the breast, so that the stabilized breast positioned within the applicator device does not substantially deform from its natural shape during the data acquisition of data of the stabilized breast positioned within the applicator device during the ultrasonic mammography examination.

26. The method of claim 25, said method including the further step of:
sealing the cup to skin near the stabilized breast positioned within the applicator device with an elastomeric sealing surface.

27. The apparatus of claim 1, wherein the cup is one of generally cylindrical, tapered cylindrical, conical, rectangular, or square shape.

28. The method of claim 8, wherein the cup is one of generally cylindrical, tapered cylindrical, conical, rectangular, or square shape.

29. The apparatus of claim 17, wherein the acoustic coupling material has a different composition than the fluid.

30. The method of claim 18, wherein the acoustic coupling material has a different composition than the fluid.

31. The apparatus of claim 17, wherein the acoustic coupling material does not come into direct contact with the stabilized breast positioned within said applicator device.

32. The method of claim 18, wherein the acoustic coupling material does not come into direct contact with the stabilized breast positioned within the applicator device.

33. The apparatus of claim 17, wherein the acoustic coupling material is in direct contact with the transducer array and said applicator device.

34. The method of claim 18, said method including the further step of:
disposing the acoustic coupling material directly in contact with the transducer array and the applicator device.

35. The apparatus of claim 1, wherein said applicator device is made from a material comprising a polymer.

36. The apparatus of claim 1, wherein said applicator device has a characteristic selected from a group of characteristics consisting of is cleanable, sterilizable and reusable.

37. The method of claim 8, wherein the applicator device is made from a material comprising a polymer.

38. The method of claim 8, wherein the applicator device has a characteristic selected from a group of characteristics consisting of cleanable, sterilizable, and reusable.

39. The apparatus of claim 17, wherein the acoustic coupling material comprises a viscous couplant.

40. The method of claim 18, wherein the acoustic coupling material comprises a viscous couplant.

41. The apparatus of claim 1, wherein said applicator device further comprises a disposable coupler for the transducer array.

42. The method of claim 8, wherein the applicator device further comprises a disposable coupler for the transducer array.

43. The apparatus of claim 1, wherein said applicator device comprises second opening through which said applicator device is filled with the fluid.

44. The method of claim 8, said fluid introduction step includes;
introducing the fluid through second opening in the applicator device through which the applicator device is filled with the fluid.

45. The apparatus of claim 1, wherein the transducer array is a single transducer array.

46. The method of claim 8, wherein the transducer array is a single transducer array.

47. The apparatus of claim 1, wherein said applicator device is a flexible bag for conforming (i) the second side thereof to the stabilized breast positioned within said applicator device and (ii) the first side thereof to the contour of the transducer array.

48. The method of claim 8, wherein the applicator device is a flexible bag for conforming (i) the second side thereof to the stabilized breast positioned within the applicator device and (ii) the first side thereof to the contour of the transducer array.

49. The method of claim 48, said method including the further step of:
filling the flexible bag with a second fluid to stabilize the breast positioned within the flexible bag, so that the stabilized breast positioned within the flexible bag does not substantially deform from its natural shape during the data acquisition of data of the stabilized breast positioned within the flexible bag during the ultrasonic mammography examination.

* * * * *